US007951603B2

(12) United States Patent
Amano

(10) Patent No.: US 7,951,603 B2
(45) Date of Patent: May 31, 2011

(54) METHOD OF MASS SPECTROMETRIC ANALYSIS OF SACCHARIDES WITH ALDEHYDE GROUPS USING LABELS CONTAINING A PYRENE RING AND A HYDRAZIDE GROUP

(75) Inventor: Junko Amano, Tokyo (JP)

(73) Assignee: The Noguchi Institute, Tokyo (JP)

( * ) Notice: Subject to any disclaimer, the term of this patent is extended or adjusted under 35 U.S.C. 154(b) by 838 days.

(21) Appl. No.: 11/884,778

(22) PCT Filed: Mar. 23, 2006

(86) PCT No.: PCT/JP2006/305800
§ 371 (c)(1),
(2), (4) Date: Aug. 21, 2007

(87) PCT Pub. No.: WO2006/109485
PCT Pub. Date: Oct. 19, 2006

(65) Prior Publication Data
US 2008/0138908 A1    Jun. 12, 2008

(30) Foreign Application Priority Data

Mar. 31, 2005  (JP) .................................. 2005-104180

(51) Int. Cl.
*G01N 33/00* (2006.01)
(52) U.S. Cl. .......................................... 436/94; 436/173
(58) Field of Classification Search .................. None
See application file for complete search history.

(56) References Cited

U.S. PATENT DOCUMENTS 5,272,260 A * 12/1993 Pope et al. ................... 536/18.1
5,668,272 A * 9/1997 Prasad et al. ................. 536/55.3

FOREIGN PATENT DOCUMENTS

JP    A 2004-317398    11/2004
WO   WO 2004/092739 A1   10/2004

OTHER PUBLICATIONS

Morelle et al. "The Mass Spectrometric Analysis of Glycoproteins and their Glycan Structures", Current Analytical Chemistry, 2005, v. 1, pp. 29-57.*
Linnemayr, K. et al., "Matrix-assisted Laser Desorption/Ionization Time-of-flight and Nano-electrospray Ionization Ion Trap Spectrometric Characterization of 1-Cyano-2-substituted-benz[f]isoindole Derivatives of Peptides for fluorescence Detection", Journal of Mass Spectrometry, Apr. 1999, vol. 34, No. 4, pp. 427-434.

(Continued)

Primary Examiner — Yelena G Gakh
(74) Attorney, Agent, or Firm — Oliff & Berridge, PLC

(57) ABSTRACT

An object of the invention is to provide a method for enabling $MS^n$ (n>) analysis of a trace amount of a sample and easily and rapidly obtaining structural information by identifying a bonding position of the labeling compound in a molecule with the $MS^n$ (n>) analysis. According to the present invention, by labeling a particular moiety of the molecule in a stable manner, ions are easily generated and stabilized, thereby improving sensitivity of the MS. The amount of precursor ions generated in this manner is an amount enough to carry out the $MS^n$ (n>1) analysis and to generate structure-specific ions with high reproducibility. The structural information can be easily and rapidly obtained with high sensitivity.

4 Claims, 13 Drawing Sheets

OTHER PUBLICATIONS

Sturrock, E. et al., "Assignment of Free and Disulfide-Bonded Cysteine Residues in Testis Angiotensin-Converting Enzyme: Implications", Biochemistry, American Chemical Society, Jan. 1, 1996, vol. 35, No. 29, pp. 9560-9566, Easton, PA.; US.

Monsarrat, B. et al., "Characterization of mannooligosaccharide caps in mycobacterial lipoarabinomannan by capillary electrophoresis/electrospray mass spectrometry", Glycobiology, vol. 9, No. 4, Apr. 1999, pp. 335-342.

Suzuki, H. et al., "Analysis of 1-Aminopyrene-3,6,8-trisulfonate-Derivatized Oligosaccharides by Capillary Electophoresis with Matrix-Assisted Laser Desorption/Ionization Time-of-Flight Mass Spectrometry", Analytical Chemistry, American Chemical Society, vol. 69, No. 22, Nov. 15, 1997, pp. 4554-4559, Columbus, US.

Daisuke Sugahara et al., "Pyrene Hyoshikiho ni yoru O Ketsugogata Tosa no Kozo Kaiseki," Dai 23 Kai, The Japanese Society of Carbohydrate Research Nenkai Yoshishu, Jul. 25, 2002, p. 123.

Daisuke Sugahara et al., "Fluorescence Labeling of Oligosaccharides Useful in the Determination of Molecular Ineractions," Analytical Sciences, Jan. 2003, vol. 19, pp. 167-169.

David J. Harvey, "Collision-induced fragmentation of negative ions from N-linked glycans derivatized with 2-aminobenzoic acid," Journal of Mass Spectrometry, 2005; 40: pp. 642-653.

David J. Harvey, Fragmentation of Negative Ions from Carbohydrates: Part 3. Fragmentation of Hybrid and Complex N-Linked Glycans, American Society of Mass Spectrometry, 2005; 16, pp. 647-659.

Li et al.; A simple photo-affinity labeling protocol; Chem. Comm.; 1999; pp. 365-366.

Sandra et al; "Characterization of Cellobiohydrolase In-Glycans and Differentiation of Their Phosphorylated Isomers by Capillary Electrophoresis-Q-Trap Mass Spectrometry"; Analytical Chemistry; Oct. 1, 2004; 76-19; pp. 5878-5886.

Morelle et al.; "Structural Analysis of O-Linked Oligosaccharide-Alditols by Electrospray-Tandem Mass Spectrometry after Mild Periodate Oxidation and Derivatization with 2-Aminopyridine"; Analytical Biochemistry; 259-1; May 15, 1998; pp. 16-27.

* cited by examiner

METHOD OF MASS SPECTROMETRIC ANALYSIS OF SACCHARIDES WITH ALDEHYDE GROUPS USING LABELS CONTAINING A PYRENE RING AND A HYDRAZIDE GROUP

TECHNICAL FIELD

The present invention relates to a method for mass spectrometry for a molecule, a spectrum obtained by the method for mass spectrometry, information obtained from the spectrum and a data collection in which the information has been accumulated.

BACKGROUND ART

"Mass spectrometry" is a method for obtaining structural information of a molecule, by ionizing a sample including the molecule, separating the ionized molecule based on mass-to-charge (m/z), and detecting the molecular ions.

Detection of the molecular ions for determining the molecular weight using a mass spectrometer cannot afford detailed structural information for molecules such as saccharides, oligosaccharides (saccharide chains), proteins (including peptide), proteins modified by saccharides (including glycopeptides (peptide modified by saccharides)), nucleic acids and glycolipids, because of possible structural isomers having the same molecular weight and composition.

Therefore, $MS^n$ (n>1) analysis is carried out. "$MS^n$ (n>1) analysis" is an analysis method for obtaining the structural information of a molecule by the steps of ionizing a biomolecule, selecting precursor ions, detecting product ions generated by post source decay (PSD), in source decay (ISD), tandem mass and the like, or alternatively by the step of selecting precursor ions from the product ions having been generated, repeating the same measurement.

In order to carry out the $MS^n$ (n>1) analysis, it is necessary to generate a sufficient amount of parent ions ($[M+Na]^+$, $[M+H]^+$, $[M-H]^-$ and the like) which become the precursor ions. However, it is difficult to obtain a sufficient amount of the parent ions for the molecules originated from the biological samples, since it is hard for such molecule as-is to be ionized sufficiently. For example, when the oligosaccharide is analyzed using matrix-assisted laser desorption ionization-time of flight mass spectrometry (MALDI-TOF MS), 10 pmol or more of the oligosaccharide is required. In order to solve the problem, there is proposed a method of labeling the oligosaccharide by the use of 1-pyrenebutanoic acid hydrazide (PBH) (for example, see Nonpatent Document 1). When the oligosaccharide labeled by the method is analyzed by the MALDI-TOF MS, reduction in detection limit (that is, improvement in sensitivity of MS) is recognized in comparison with an unlabeled oligosaccharide. However, in the current state, it has been insufficient to generate the parent ions to a required level for carrying out the $MS^n$ (n>1) analysis to the biological samples in sub-pmol level.

Nonpatent Document 1: Sugahara, D. Et al., Anal. Sci, 19, 167-169 (2003)

Nonpatent Document 2: Harvey, D. J., J. Mass Spectrom., 40, 642-653 (2005)

Nonpatent Document 3: Harvey, D. J., J. Am. Soc. Mass. Spectrom., 16, 647-659 (2005)

DISCLOSURE OF THE INVENTION

An object of the invention is to carry out $MS^n$ (n>1) analysis of even a small amount of a sample, by generating a sufficient amount of parent ions and also improving the sensitivity of a MS by labeling a molecule, and thereby promoting ionization and stabilizing the generated ions. Another object of the invention is to provide a method for easily and rapidly obtaining structural information of an analyzing sample by identifying a bonding position of a labeling compound in the molecule by means of the $MS^n$ (n>1) analysis carried out by the above-mentioned method.

The present inventors of the invention have found that improvement in ionization efficiency and stabilization of the generated ions are realized by labeling a particular moiety of the molecule in a stable manner, thereby improving sensitivity of the MS. The inventors have also found that this method provides an enough amount of precursor ions to carry out the $MS^n$ (n>1) analysis and generates structure-specific ions with high reproducibility. As a result, the inventors have achieved a method for easily and rapidly obtaining the structural information with high sensitivity.

According to the present invention, the ionization efficiency as well as the sensitivity of the MS are improved, since the molecule is bonded to the compound having the fused polycyclic hydrocarbon. Accordingly, the $MS^n$ (n>1) analysis for the molecule can be readily carried out to obtain the structural information with high reliability. Moreover, according to the present invention, the structural information of the oligosaccharide and the bonding position of the oligosaccharide on a peptide can be obtained accurately. Accordingly, it is possible to provide a method for obtaining information useful in explaining functions of a glycoprotein or in explaining pathological conditions related to the glycoprotein.

DETAILED DESCRIPTION OF THE INVENTION

Figure 1A:
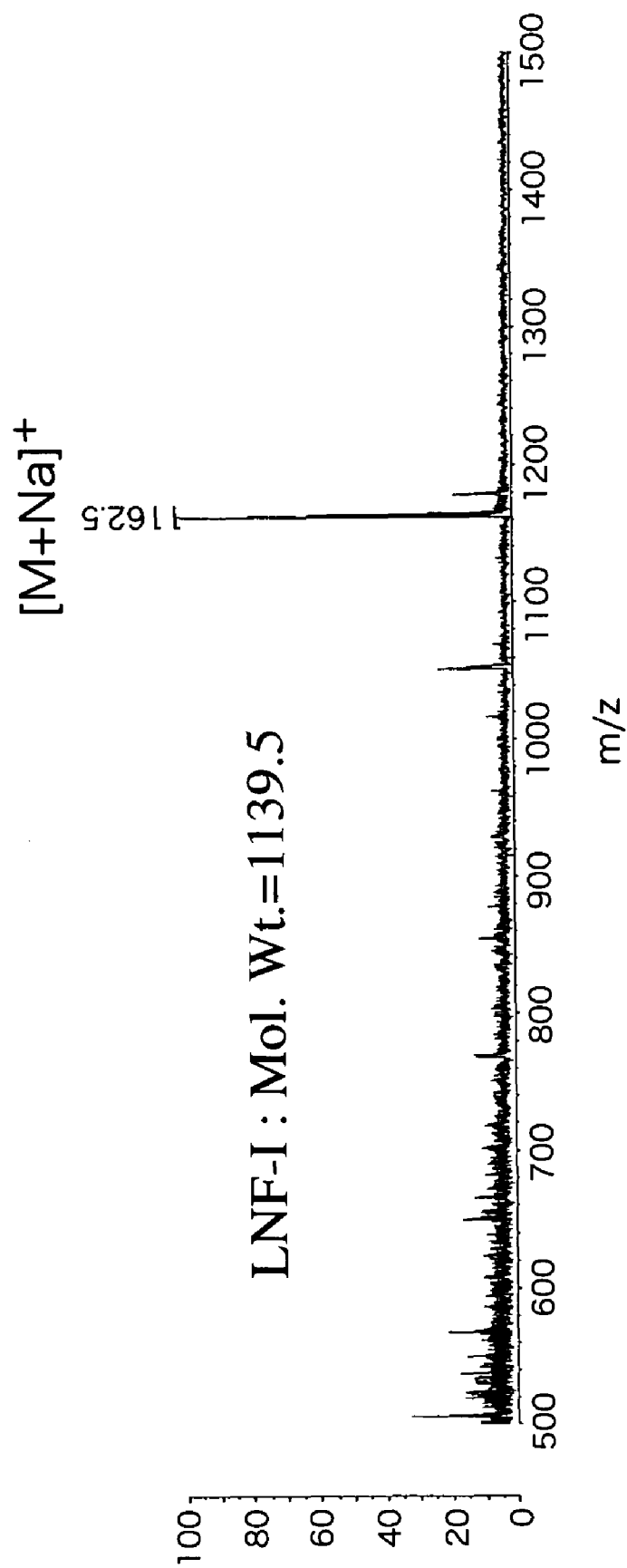
Fig. 1A is a diagram illustrating a positive-ion MALDI-TOF MS spectrum obtained from a labeled and reduced LNF-I in Example 2.

In the present invention, a molecule in a sample is labeled using a compound having fused polycyclic hydrocarbon and then $MS^n$ (n>1) analysis for the labeled molecule is carried out. The processes will be described in detail.

(1) Labeling of Molecules

"Molecule" includes saccharides, oligosaccharides, proteins, nucleic acids and glycoconjugates (glycoproteins, glycolipids and the like). In addition, the "molecule" may be prepared naturally and may be prepared chemically or enzymatically. In the present invention, the term "protein" includes a peptide, and the term "glycoprotein" includes a glycopeptide. In addition, the "molecule" may have a partial structure of the molecule included in an organism, and may be prepared by mimicking the molecule included in the organism.

As for saccharide, oligosaccharide, or when a labeled and reduced molecule is prepared by the use of the oligosaccharide which has been chemically or enzymatically liberated from glycoconjugates (hereinafter, referred to as "oligosaccharide"), condensation reaction of the aldehyde group of the reducing terminal in the saccharide with a labeling compound which is a fused polycyclic hydrocarbon derivative having a hydrazide group ($-CONHNH_2$) or an amino group is carried out to form a labeled intermediate, and then the labeled intermediate is reduced. Generally, the condensation reaction is carried out by heating the oligosaccharide and the labeling compound in an organic solvent such as methanol or DMSO, in the presence or absence of a catalyst such as acetic acid. Then, a reducing agent such as $NaCNBH_3$ and $NaBH_4$ is added and the reduction reaction is carried out at a room temperature or while applying heat. Alternatively, the reducing agent may coexist in the condensation reaction solution in the first step. In a known method in which the labeling is carried out by condensing the aldehyde group in the sugar of the reducing terminal with PBH, the stability of parent ions such as $[M+Na]^+$ or $[M-N]^-$ was low and the sensitivity thereof has been lowered. However, according to the present invention, the reduction reaction is additionally carried out so that the parent ions are sufficiently generated. As a result, it is found to obtain sufficient sensitivity.

The saccharides, the oligosaccharides or the glycoconjugates containing sialic acid can be labeled by using the fused polycyclic hydrocarbon derivative having the hydrazide group, the amino group and a diazomethyl group as the labeling compound, in which a carboxy group of the sialic acid reacts with the hydrazide group, the amino group and the diazomethyl group of the labeling compound. The reaction is carried out in the presence of, for example, water-soluble carbodiimide and N-hydroxysulfosuccinimide.

In addition, it is possible to generate the aldehyde group by selectively oxidizing a $C_{7-9}$ position of the sialic acid in the saccharide, oligosaccharide or the glycoconjugate containing the sialic acid, with periodic acid. The $C_{7-9}$ position of the sialic acid can be selectively oxidized by the reaction in a $NaIO_4$ solution of 5 mM at 0° C. for 10 to 20 minutes. Using the labeling compound which is the fused polycyclic hydrocarbon derivative having the hydrazide group or the amino group, the labeled intermediate is generated by carrying out the condensation reaction between the aldehyde group generated by the selective oxidization and the hydrazide group or the amino group of the labeling compound as described above. Then, it is possible to obtain the labeled and reduced molecule by reducing the labeled intermediate.

Most of the saccharides, the oligosaccharides or the glycoconjugates contain galactose on the non-reducing terminal. It is possible to generate the aldehyde group by specifically oxidizing a $C_6$ position of the galactose on the non-reducing terminal with galactose oxidase. The enzymatic reaction can be carried out in neutral buffer solution at a room temperature for 2 hours. Using the labeling compound which is the fused polycyclic hydrocarbon derivative having the hydrazide group or the amino group, the labeled intermediate is generated by carrying out the condensation reaction between the aldehyde group generated by the above-mentioned enzymatic oxidization and the hydrazide group or the amino group of the labeling compound as described above. Then, it is possible to obtain the labeled and reduced molecule by reducing the labeled intermediate.

The above methods of labeling the sialic acid and the galactose can be applied to the sialic acid and the galactose on the glycoprotein molecule (including the glycopeptide). In this case, the ionization efficiency of the molecule is increased and the sensitivity of the MS becomes high, since the glycoprotein molecule can be labeled. Moreover, in the present invention, it is possible to identify the bonding position of the oligosaccharide on the peptide chain of the protein by carrying out the $MS^n$ (n>1) analysis to the protein including the oligosaccharide, since the oligosaccharide on the molecule can be labeled without liberating the oligosaccharide. In addition, it is possible to obtain the structural information of the oligosaccharide by carrying out the $MS^n$ (n>1) analysis to the labeled oligosaccharide moiety. In explaining the function of the glycoprotein, identification of the position of the oligosaccharide added on the peptide chain and the structure of the oligosaccharide is extremely important. In most cases, it is necessary to clarify the correspondence between the position and the structure of the oligosaccharide, since the plurality of oligosaccharides having structures different from one another are bonded to the plurality of bonding positions on the peptide chain. It is possible to obtain such information by the technique of the present invention.

The protein (including the peptide) and the glycoprotein (including the glycopeptide) can be labeled using the carboxy group, the amino group or a SH group contained in the protein and the glycoprotein. When the carboxy group is used in the labeling, a fused polycyclic hydrocarbon derivative having the hydrazide group, the amino group, a diazomethyl group and the like can be used as the labeling compound, such groups being reacted with the carboxy group in the protein or the glycoprotein to obtain the labeled molecule. When the amino group is used in the labeling, a fused polycyclic hydrocarbon derivative having a succinimidyl ester group, a sulfonyl chloride group and the like can be used as the labeling compound, such groups being reacted with the amino group in the protein or the glycoprotein to obtain the labeled molecule. When the SH group which is a cysteine residue contained in the protein or the glycoprotein is used in the labeling, a fused polycyclic hydrocarbon derivative having an iodine group (—I) and the like can be used as the labeling compound and the iodine group being reacted with the SH group in the protein or the glycoprotein to obtain the labeled molecule.

(2) Labeling Compound

The labeling compound is the fused polycyclic hydrocarbon derivative. "Fused polycyclic hydrocarbon derivative" is a compound having a fused polycyclic hydrocarbon moiety such as naphthalene, anthracene and pyrene, a reactive functional group capable of being bonded to an analyzing target molecule and a spacer moiety connecting the reactive functional group to the fused polycyclic hydrocarbon moiety if necessary.

The labeling compound preferably used in the present invention is a pyrene derivative compound. "Pyrene derivative compound" is a compound having a pyrene ring, a reactive functional group capable of being bonded to an analyzing target molecule and a spacer moiety connecting the reactive functional group to the pyrene ring if necessary. Specifically, examples of the pyrene derivative compound can include 1-pyrenebutanoic acid hydrazide (PBH), 1-pyreneacetic acid hydrazide, 1-pyrenepropionic acid hydrazide, 1-pyreneacetic acid succinimidyl ester, 1-pyrenepropionic acid succinimidyl ester, 1-pyrenebutanoic acid succinimidyl ester, N-(1-pyrenebutanoyl) cysteic acid succinimidyl ester, N-(1-pyrenyl) iodoacetamide, N-(1-pyrenyl) iodomaleimide, N-(1-pyrenemethyl) iodoacetamide, 1-pyrenemethyl iodoacetate, aminopyrene, 1-pyrenemethylamine, 1-pyrenepropylamine, 1-pyrenebutylamine, 1-pyrenesulfonyl chloride or the like. PBH is preferable.

(3) Method for Mass Spectrometry

"Method for mass spectrometry" is a method of ionizing a sample including a molecule using ionization methods such as Matrix-Assisted Laser Desorption Ionization (MALDI), Laser Desorption (LD), Fast Atom Bombardment ionization (FAB), ElectroSpray Ionization (ESI) and Atmospheric Pressure Chemical Ionization (APCI), subsequently separating the ionized molecule based on mass-to-charge (m/z) and detecting the molecular ions using Time-of-Flight (TOF), Double-Focusing or Quadrupole-Focusing.

In the MALDI method, bonding of the fused polycyclic hydrocarbon to the molecule improves the ionization efficiency. In addition, the molecular ions are more stabilized by the labeling and reducing process.

In the ESI method, the sample solution is required to be easily vaporized. Since the materials such as the saccharides, the oligosaccharide, the protein and the glycoprotein have a high hydrophilic property, and therefore, it is difficult to dissolve the materials in solution containing an organic solvent. However, due to labeling with the fused polycyclic hydrocarbon derivative, the labeled materials are soluble in the organic solvent, and thereby the ESI method can be applied to such materials.

In the present invention, the preferable ionization method is, but not limited thereto, the ESI or the MALDI method, and more preferably the MALDI method.

The molecules, such as the saccharide, the oligosaccharide, the protein, the protein modified by the saccharides (glycoprotein), the nucleic acid and the glycolipid, include possible structural isomers having the same molecular weight and composition. Accordingly, after labeling by means of the fused polycyclic hydrocarbon derivative, and then the generation of precursor ions increases and the MS" (n>1) analysis is carried out to generate specific ions in the isomers, thereby obtaining the structural information. When the MS" (n>1) analysis is carried out to the molecule in which the oligosaccharide of the glycopeptide or the glycoprotein is labeled, the bonding position of the oligosaccharide in the molecule can be determined by selecting the product ions including the labeled portion.

A spectrum obtained by the above-mentioned mass spectrometry method according to the present invention is useful in specifying the structure of the molecule such as the saccharide, the oligosaccharide, the protein, the protein modified by the saccharides (glycoprotein), the nucleic acid and the glycolipid. The information including the structural information of the oligosaccharide moiety obtained from the spectrum and the bonding position of the oligosaccharide in the molecule provides a method for obtaining information useful in explaining functions of the molecule or pathological conditions related to the molecule. Accordingly, when a data collection which accumulates the information acquired from the spectrum obtained by the method of mass spectrometry method according to the present invention can provide the information useful in specifying the unknown molecular structure and in explaining the functions of the molecule and the pathological conditions related to the molecule, when combined with a computer system making an inquiry into the accumulated information and the method of mass spectrometry according to the present invention.

EXAMPLES

Example 1

Labeling of Oligosaccharide

Labeled and reduced oligosaccharide was obtained by labeling with a pyrene derivative compound (PBH) of lacto-N-fucopentaose I (LNF-I, a compound of chemical formula (1)) and lacto-N-fucopentaose II (LNF-II, a compound of chemical formula (2)), which are oligosaccharides having a blood group antigen H or Le$^a$, the same molecular weight and the same chemical composition and which are in relation of structural isomers.

[Chemical Formula 1]

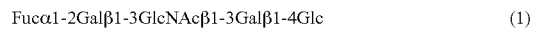
(1)

[Chemical Formula 2]

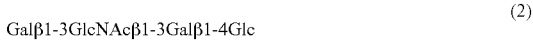
(2)

(wherein, "Gal", "Glc", "Fuc" and "GlcNAc" represent galactose, glucose, fucose and N-acetylglucosamine, respectively.)

Specifically, 1 nmol of the oligosaccharide was added to a glass reaction tube with a screw lid attached thereon, and then dried and solidified. 500 nmol of PBH was dissolved in 20 µL of methanol and added to the reaction tube. Further, 2 µL of acetic acid diluted with the methanol (acetic acid:methanol=1:8, v/v) was added to the reaction tube and the lid was screwed tightly. After stirring the mixture completely, the reaction mixture was heated at a temperature of 80° C. for 20 minutes and was neutralized by adding 1M of NaOH aqueous solution. 30 µL of 1.7M solution of NaBH$_4$ was added to the reaction mixture and reacted at a temperature of 40° C. for 30 minutes, and then, 10 µL of 1.7M solution of NaBH$_4$ was further added to the reaction mixture and reacted at a temperature of 40° C. for 30 minutes. After 400 µL of pure water and 400 µL of chloroform were added to the reaction mixture and shaken, the reaction mixture was left. The chloroform of the lower phase of the tube was removed and 400 μL of fresh chloroform was added for re-extraction. The reaction product of the upper phase was taken up, and then dried and solidified. The dried and solidified reaction product was dissolved in the pure water and passed through a Sep-pak $C_{18}$ cartridge which had been rinsed with methanol and subsequently had been rinsed with pure water. The cartridge was rinsed with the pure water, and then the reaction product was eluted with acetonitrile-pure water (acetonitrile:water=6:4, v/v). Accordingly, the LNF-I and LNF-II which were labeled with PBH and then reduced (hereinafter, respectively, referred to as the labeled and reduced LNF-I and the labeled and reduced LNF-II) were obtained. The obtained labeled and reduced LNF-I and the labeled and reduced LNF-II were stored at a temperature of −30° C. while shielding light.

Example 2

Figure 1B:
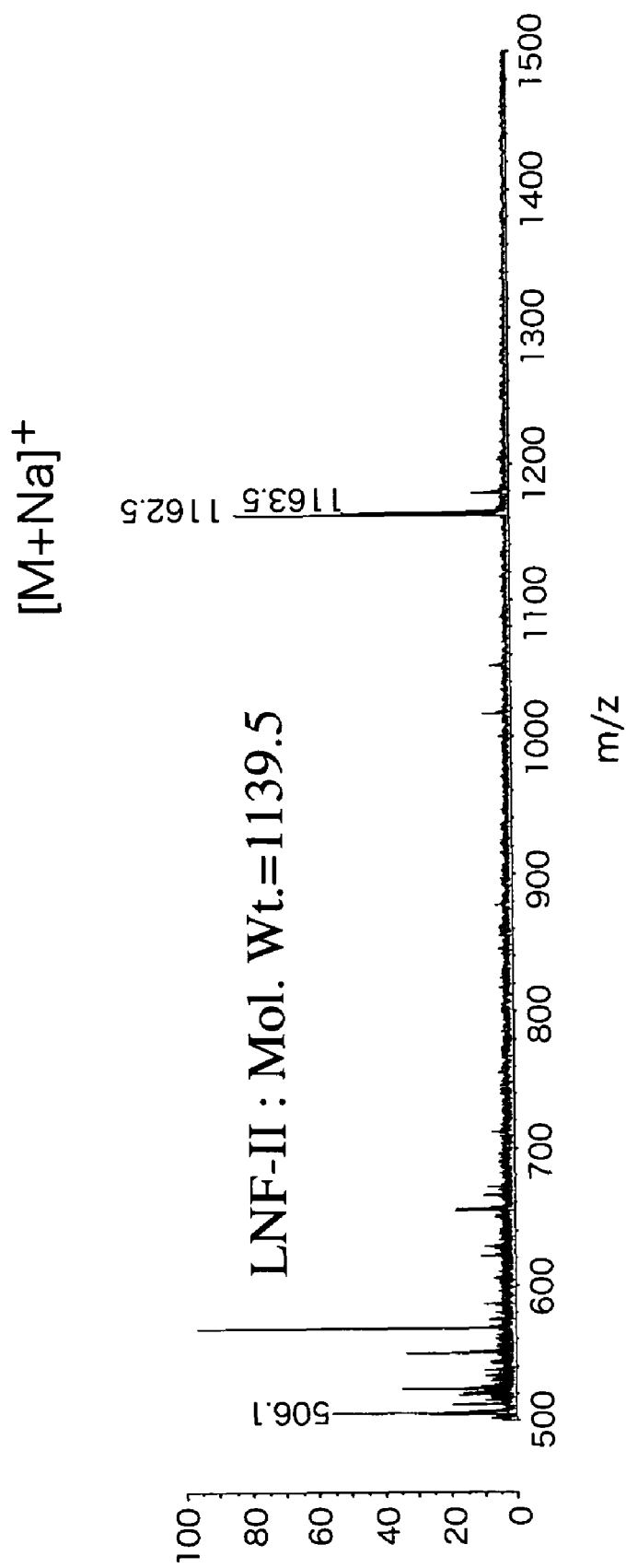
FIG. 1B is a diagram illustrating a positive-ion MALDI-TOF MS spectrum obtained from a labeled and reduced LNF-II in Example 2.

The labeled and reduced LNF-I and the labeled and reduced LNF-II obtained in Example 1 were dissolved in the pure water respectively and 1 pmol of the labeled and reduced oligosaccharides were applied to a MALDI target plate. Matrix solution, in which 2,5-dihydroxybenzoic acid (DHBA) was dissolved in 40% acetonitrile-pure water, was mixed with the labeled oligosaccharide solutions on the target plate, and then dried and solidified. MS analysis was carried out using MALDI-TOF MS instrument (Axima-CFR plus (Shimadzu/Kratos)). FIG. 1A shows the spectrum obtained from the labeled and reduced LNF-I, and FIG. 1B shows the spectrum obtained from the labeled and reduced LNF-II. As shown in FIGS. 1A and 1B, a sufficient amount of $[M+Na]^+$ having an m/z of 1162.5 was detected from both of the labeled and reduced oligosaccharides.

Figure 2A:
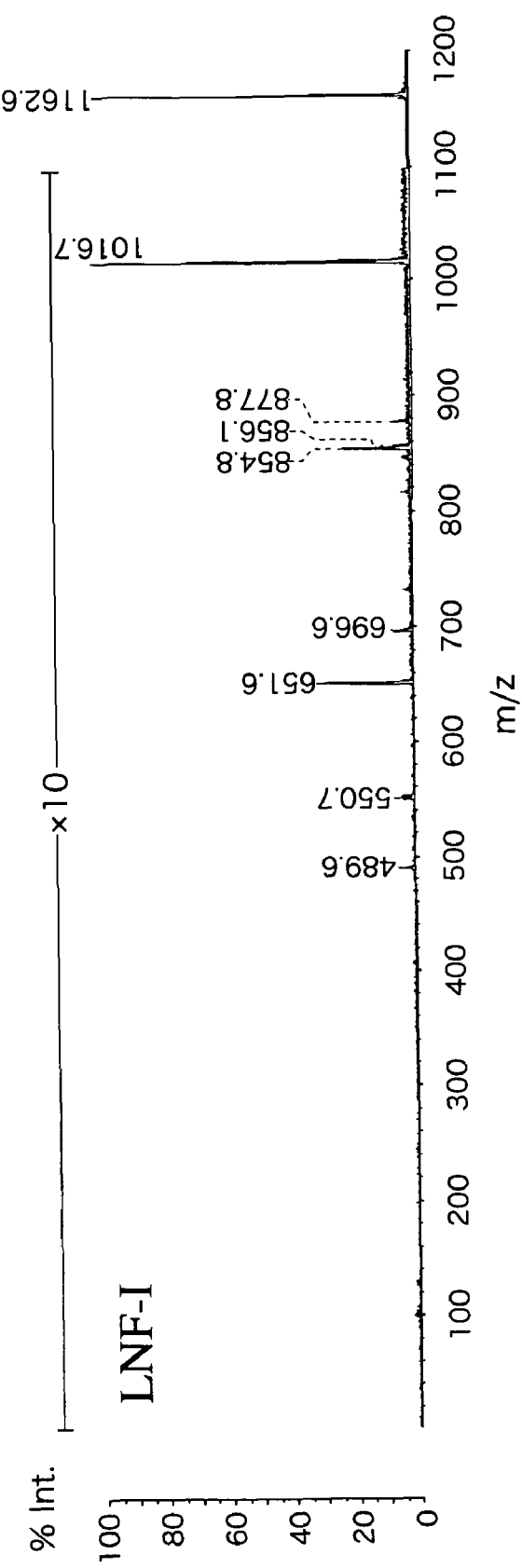
FIG. 2A is a diagram illustrating a PSD-MS/MS spectrum obtained from the parent ion $[M+Na]^+$ of the labeled and reduced LNF-I in Example 2.
Figure 2B:
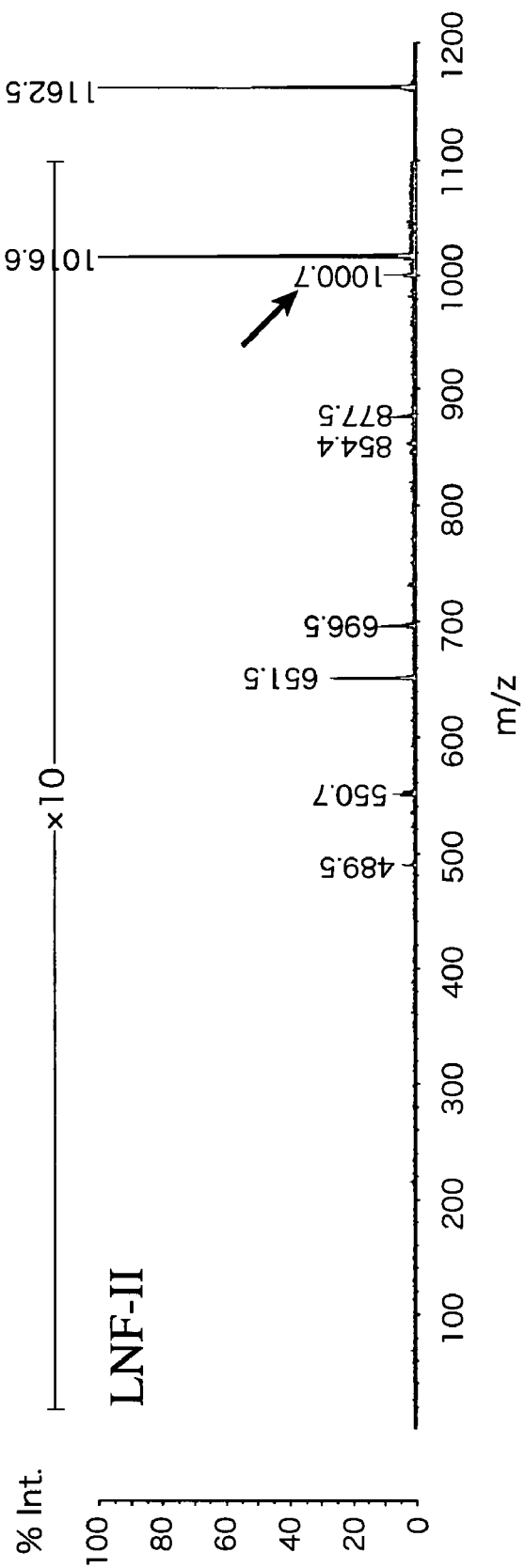
FIG. 2B is a diagram illustrating a PSD-MS/MS spectrum obtained from the parent ion $[M+Na]^+$ of the labeled and reduced LNF-II in Example 2.

Next, PSD-MS/MS (that is, $MS^2$) analysis was carried out by using the above-obtained parent ions as precursor ions. FIG. 2A shows the spectrum obtained from the labeled and reduced LNF-I parent ions, and FIG. 2B shows the spectrum obtained from the labeled and reduced LNF-II parent ions. As shown in FIGS. 2A and 2B, an ion having an m/z of 1000 (in FIG. 2B, the peak indicated by the arrow) was detected from the labeled and reduced LNF-II, however it was not detected from the labeled and reduced LNF-I. That is, the labeled and reduced LNF-I and the labeled and reduced LNF-II, which are isomers, can be distinguished from each other, by the structure-specifically generated ion.

Example 3

MS analysis was carried out to the labeled and reduced LNF-I and LNF-II obtained in Example 1, using an ESI-MS instrument connected to a LC pump (LCQ (Thermo Electron)). The labeled and reduced LNF-I and LNF-II were each dissolved in 50% acetonitrile-pure water to make 1 pmol/mL of solution, and 1 μm of the solution was injected to the ESI-MS instrument. In addition, 90% acetonitrile-pure water/pure water (90% acetonitrile-pure water:pure water=50:50) with 0.1% of TFA was used as a mobile phase and the flow rate of the mobile phase was 3 mL/min.

Figure 3A:
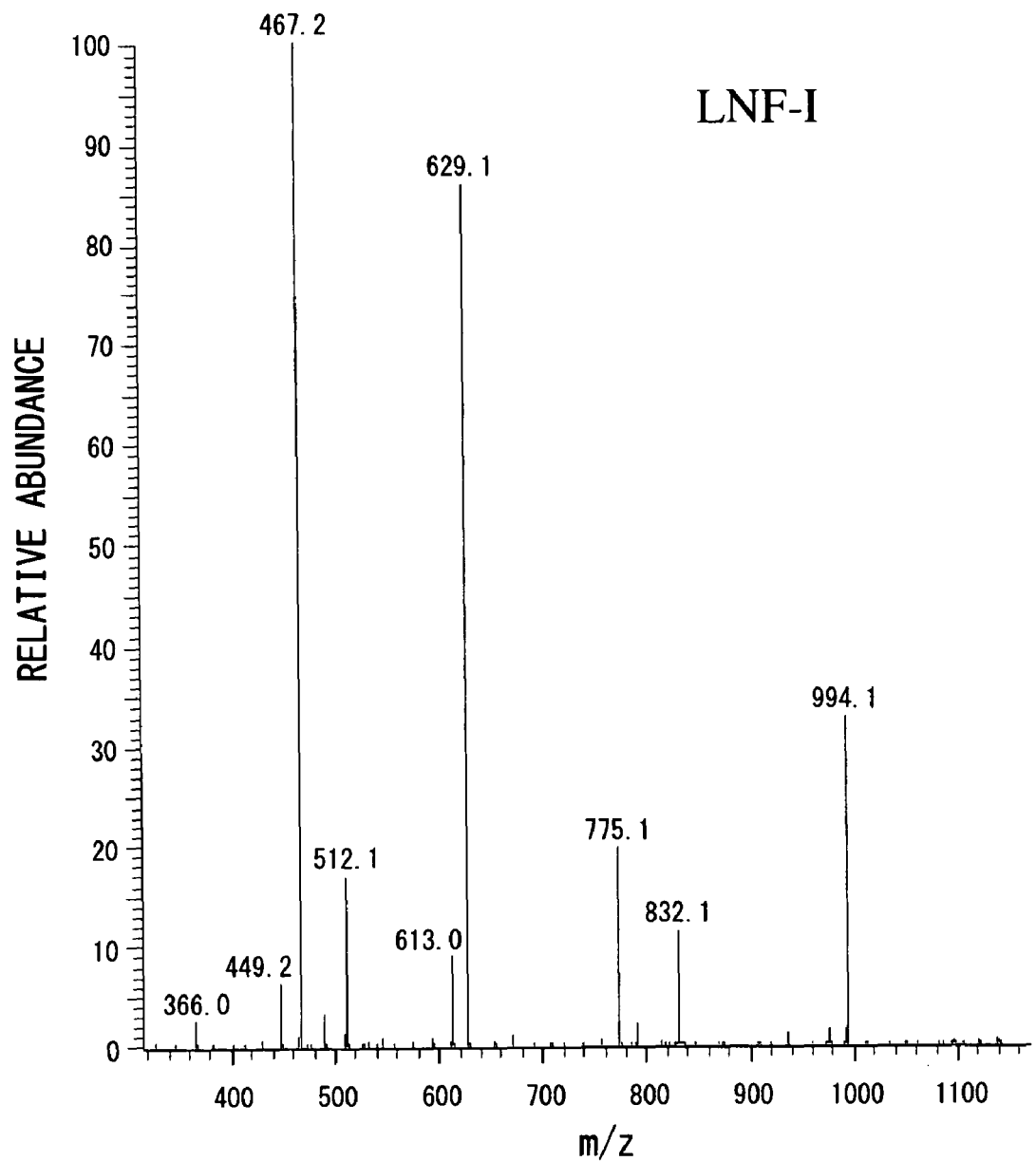
FIG. 3A is a diagram illustrating an ESI-MS/MS spectrum obtained from the parent ion $[M+H]^+$ of the labeled and reduced LNF-I in Example 3.
Figure 3B:
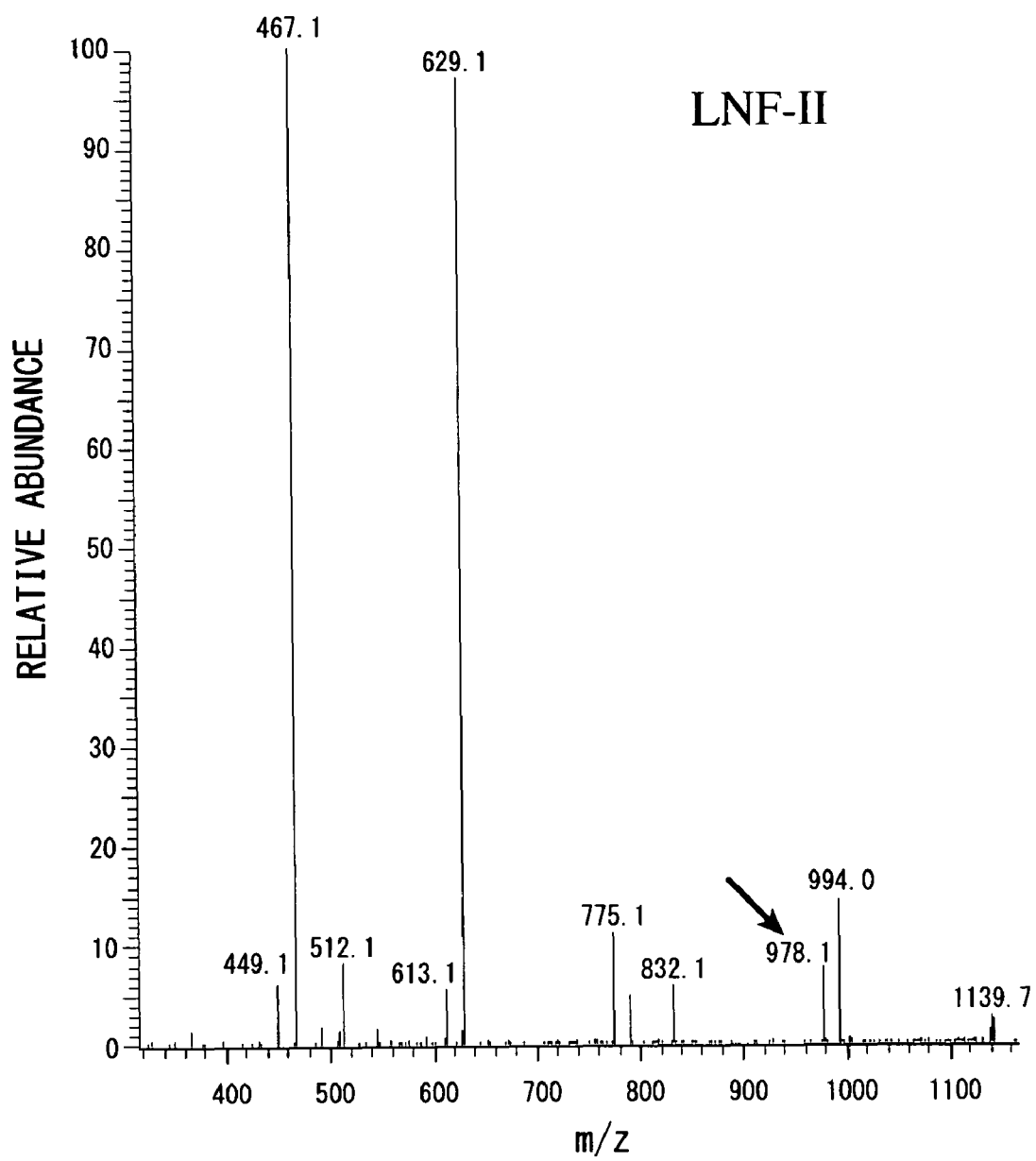
FIG. 3B is a diagram illustrating an ESI-MS/MS spectrum obtained from the parent ion $[M+H]^+$ of the labeled and reduced LNF-II in Example 3.

A parent ion $[M+H]^+$ having an m/z of 1140.5 obtained by the MS analysis was selected as the precursor ion, and MS/MS measurement was carried out. FIG. 3A shows the spectrum obtained from the labeled and reduced LNF-I parent ions and FIG. 3B shows the spectrum obtained from the labeled and reduced LNF-II parent ions. As shown in FIGS. 3A and 3B, an ion having an m/z of 978 (in FIG. 3B, the peak indicated by the arrow) was detected specifically from the labeled and reduced LNF-II only, thereby distinguishing both of the isomers from each other.

Comparative Example 1

To the LNF-I and LNF-II, the procedure of Example 1 was repeated except that the reduction with the reducing agent $NaBH_4$ was not carried out, thereby obtaining the labeled LNF-I and the labeled LNF-II labeled by PBH. The MALDI-TOF MS analysis was carried out to the labeled LNF-I and the labeled LNF-II in accordance with the procedure described in Example 2. However, it was difficult to carry out the $MS^n$ (n>1) analysis, since the ion strength of the parent ions obtained from the labeled LNF-I and the labeled LNF-II was one-tenth or less in comparison with those of the labeled and reduced LNF-I and the labeled and reduced LNF-II.

Example 4

The following compounds (3) to (5) were labeled and reduced by means of the pyrene derivative compound (PBH) in accordance with the same manner as Example 1, and then negative-ion MALDI-TOF MS/MS measurement was carried out using MALDI-QIT-TOF MS (Axima-QIT (Shimadzu/Kratos)) equipped with a quadrupole ion trap (QIT). In this example, the parent ions of the compounds were used as the precursor ions in the MS measurement of the second step.

[Chemical Formula 3]

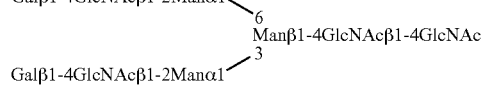
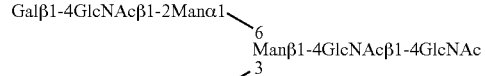
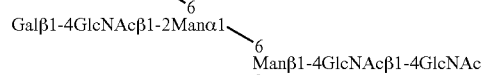

(wherein "Man" represents mannose.)

Figure 4:
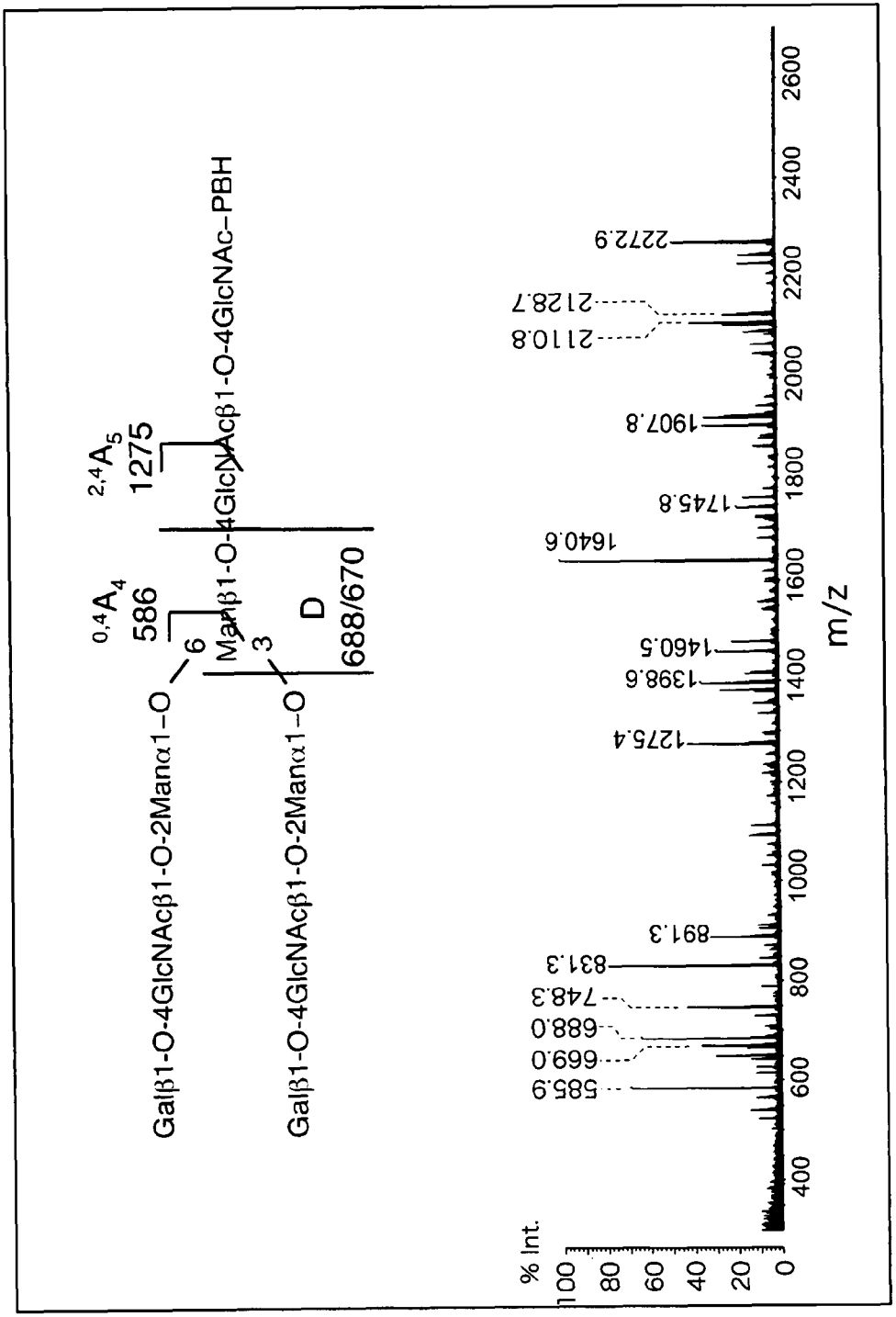
FIG. 4 is a diagram illustrating a negative-ion MALDI-TOF MS/MS spectrum of Compound (3), with positions of fragmentation thereof, obtained in Example 4.
Figure 5:
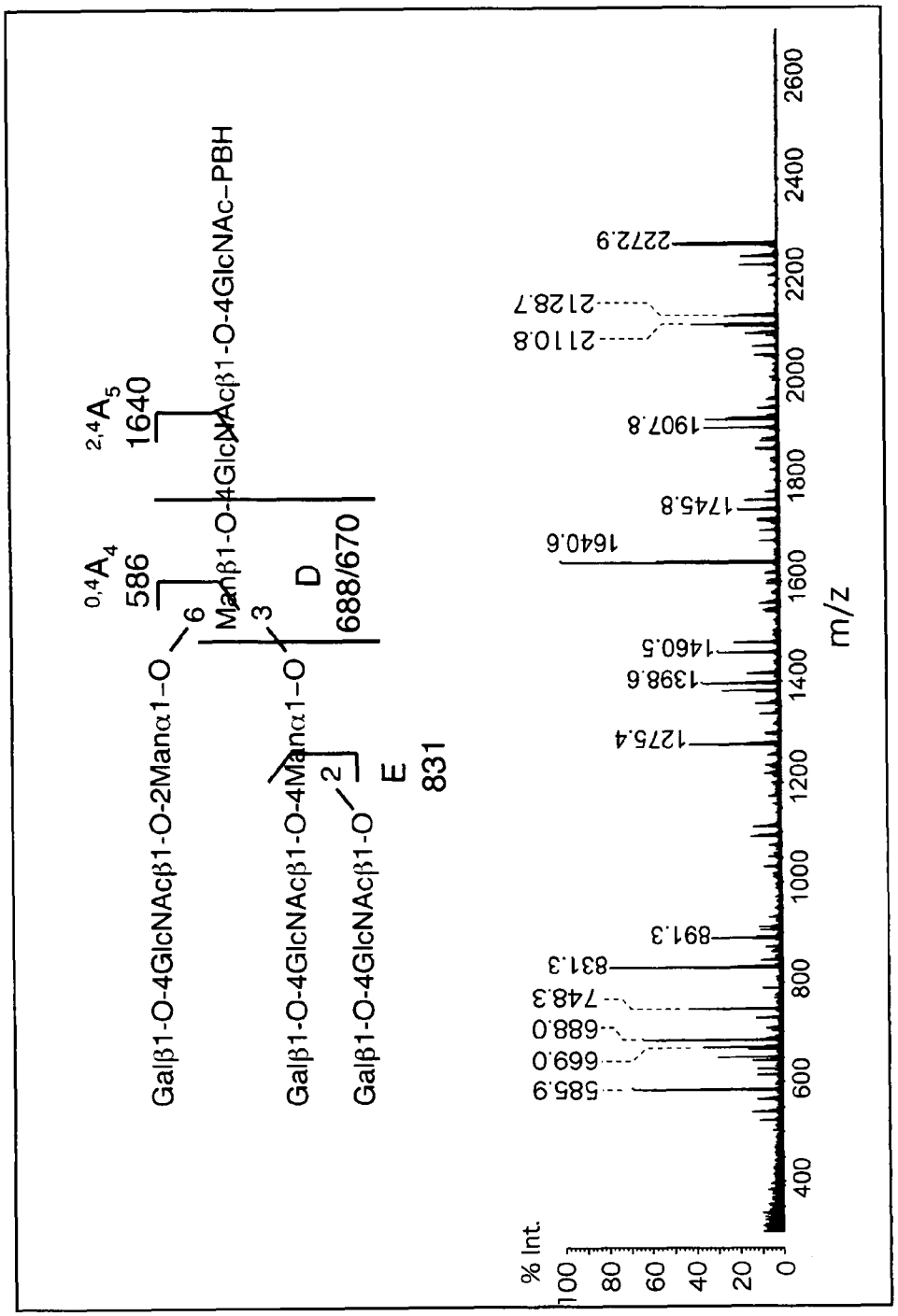
FIG. 5 is a diagram illustrating a negative-ion MALDI-TOF MS/MS spectrum of Compound (4), with positions of fragmentation thereof, obtained in Example 4.
Figure 6:
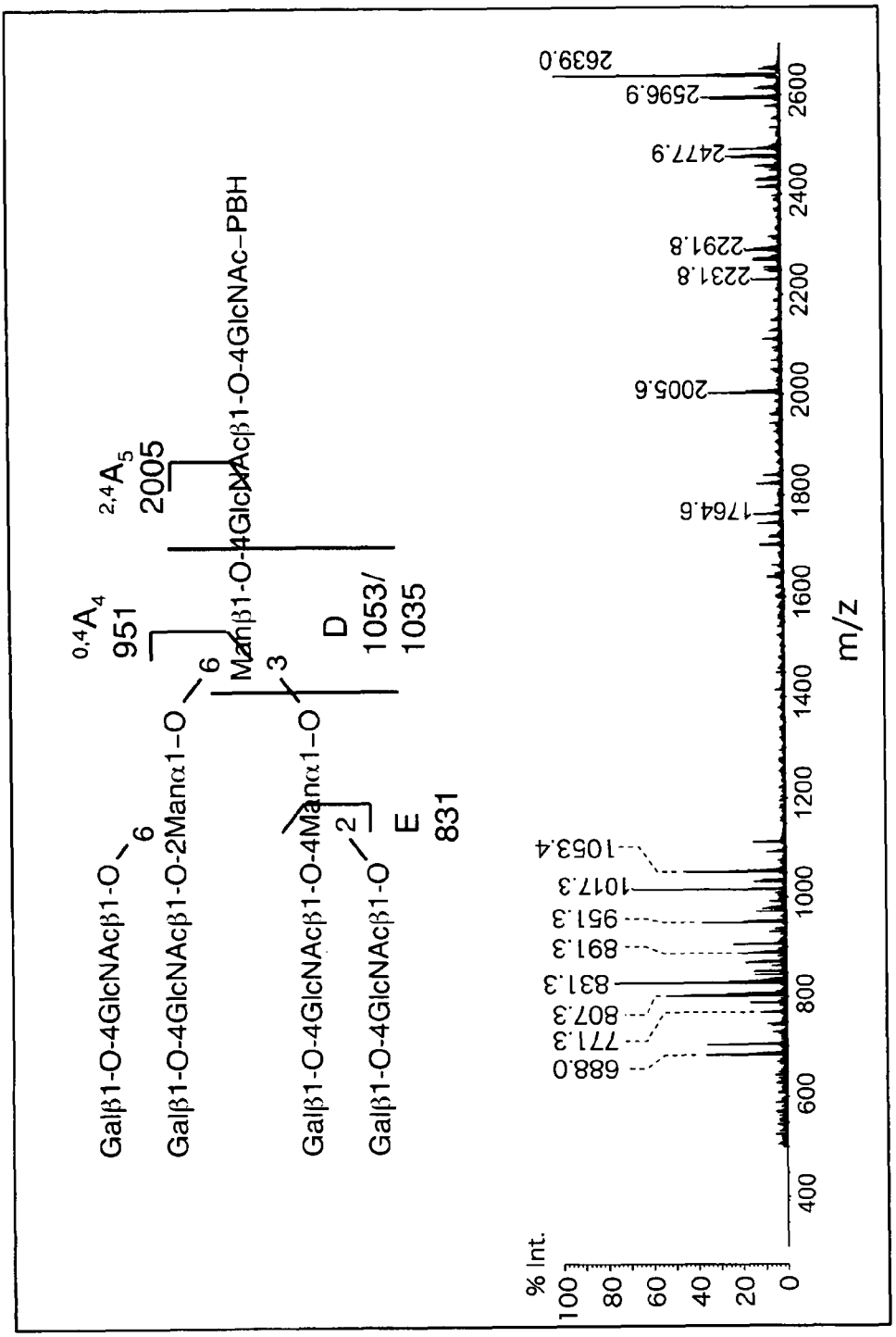
FIG. 6 is a diagram illustrating a negative-ion MALDI-TOF MS/MS spectrum of Compound (5), with positions of fragmentation thereof, obtained in Example 4.

FIGS. 4 to 6 show the spectra obtained by the measurement of the compounds (3) to (5) with positions of fragmentation thereof (in the figures, O atoms of glycoside bonds are shown in order to clarify the fragment positions. The following figures are the same). As shown in FIGS. 4 to 6, $^{0,4}A_4$, $^{2,4}A_5$, D and E type ions were generated, which are fragment ions specific to their structures. The detection of such ions in the negative-MS/MS measurement is effective in the structure identification (for example, see Nonpatent Documents 2 and 3). For example, in Nonpatent Document 2, wherein the reducing and labeling by means of 2-aminobenzoate is carried out, only the $^{0,4}A_4$ ion is detected. In Nonpatent Document 3, $^{2,4}A_5$, D and E type ions are detected using an unlabeled oligosaccharide. It can be seen that it is possible to generate more kinds of the structure-specific ions, using the reducing and labeling method with the pyrene derivative compound according to the present invention, in comparison with the above documents. Accordingly, the method according to the present invention is not only useful for obtaining more information to identify the structure but also enabling the high-sensitivity detection, by means of the reducing and labeling technique using the pyrene derivative compound.

Example 5

The following compound (6) was labeled and reduced using the PBH in accordance with the same manner as Example 1, and then the negative-ion MALDI-TOF MS/MS measurement was carried out using the MALDI-QIT-TOF MS (Axima-QIT (Shimadzu/Kratos)).

[Chemical Formula 4]

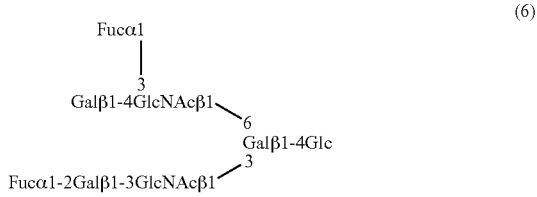

(6)

Figure 7:
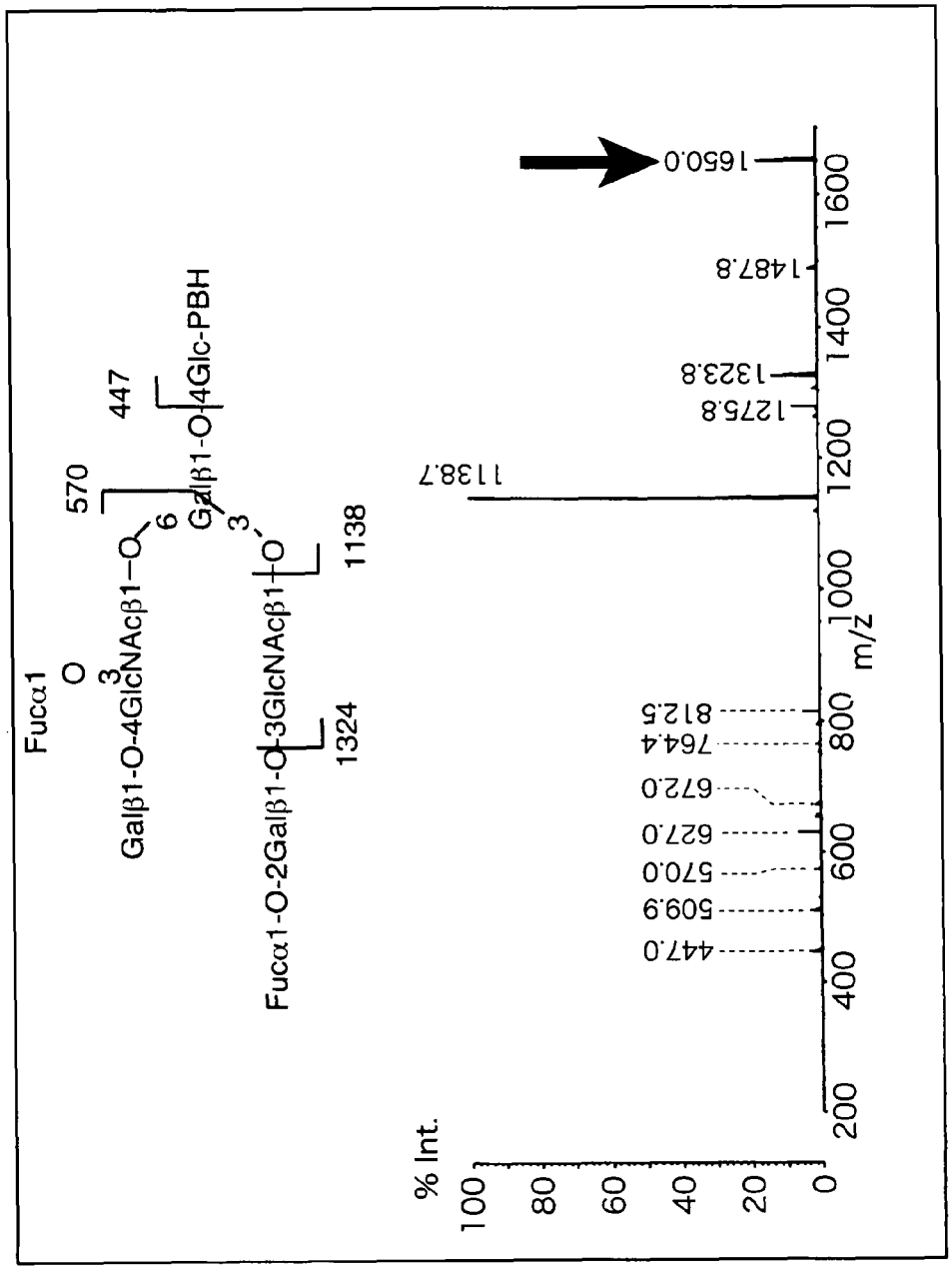
FIG. 7 is a diagram illustrating and a negative-ion MALDI-TOF MS/MS spectrum of Compound (6), with positions of fragmentation thereof, obtained in Example 5.

In the MS measurement of the second step, an [M–H]⁻ ion having an m/z of 1650 was used as the precursor ion. FIG. 7 shows the spectrum obtained from the measurement of the compound (6) with positions of fragmentation thereof. The arrow shown in FIG. 7 indicates the peak of the precursor ion. In the spectrum shown in FIG. 7, there were detected an ion having an m/z of 570 showing that fucose exists on the side chain at 6 position and an ion having an m/z of 1324 showing that the Fucα1-O-2Gal structure was eliminated.

Figure 8:
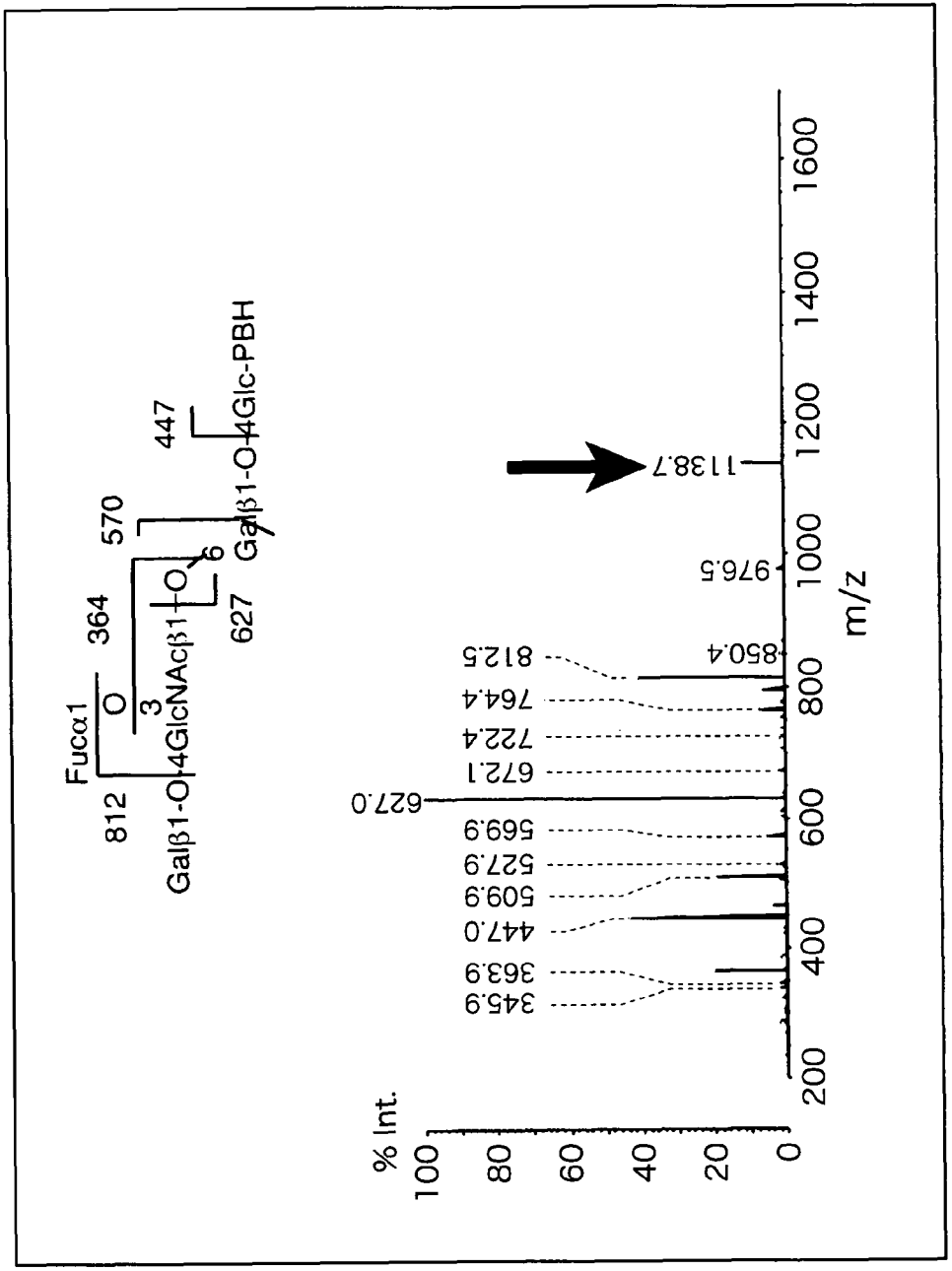
FIG. 8 is a diagram illustrating a negative-ion MALDI-TOF $MS^3$ spectrum of a precursor ion having a mass-to-charge ratio (m/z) of 1138 obtained by a negative-ion MALDI-TOF MS/MS analysis for Compound (6), with positions of fragmentation thereof, obtained in Example 5.

Using an ion having an m/z of 1138 (the ion of the eliminated side chain at 3 position, Fucα1-2Galβ1-3GlcNAc) as the precursor ion, negative-ion MALDI-TOF MS$^3$ measurement was carried out. FIG. 8 shows the spectrum obtained from the measurement with positions of fragmentation of the precursor ion. The arrow in the spectrum shown in FIG. 8 indicates the peak of the precursor ions. In the spectrum shown in FIG. 8, there were detected an ion having an m/z of 364 to be generated when the Galβ1-4(Fucα1-3)GlcNAc structure exists, as well as an ion having an m/z of 570 showing that fucose exists on the side chain at 6 position.

The structure of the compound (6) can be easily identified from the measurement results of the negative-ion MALDI-TOF MS/MS and the negative-ion MALDI-TOR MS$^3$.

Example 6

The LNF-I (compound (1)) and the LNF-II (compound (2)), which have a blood group antigen H or Le$^a$ and are in relation of structural isomers, were labeled by introducing the pyrene derivative compound to galactose of the non-reducing terminal, rather than the glucose of the reducing terminal. Hereinafter, the method will be described in detail. First, the LNF-I and the LNF-II were left in sodium borohydride solution with 10 mg/ml of concentration for two hours to be reduced such that the glucose of the reducing terminal was not labeled by the pyrene derivative compound. Next, galactose oxidase (6 units) was added and the reaction solution was left at a temperature of 37° C. during one night, so that the galactose was oxidized to generate an aldehyde group. After completing the reaction, the enzyme was denatured by the methanol and the reaction solution was filtered using a filter to remove the enzyme. The remaining solution was dried and solidified and the residue was labeled with PBH and reduced in accordance with the same manner as Example 1.

Using the MALDI-QIT-TOFMS (Axima-QIT (Shimadzu/Kratos)), the negative-ion MS analysis was carried out to the reaction product. As a result, an [M–H]⁻ ion having an m/z of 1138 were obtained and it was confirmed that both of the LNF-I and LNF-II were labeled with PBH and reduced.

Figure 9:
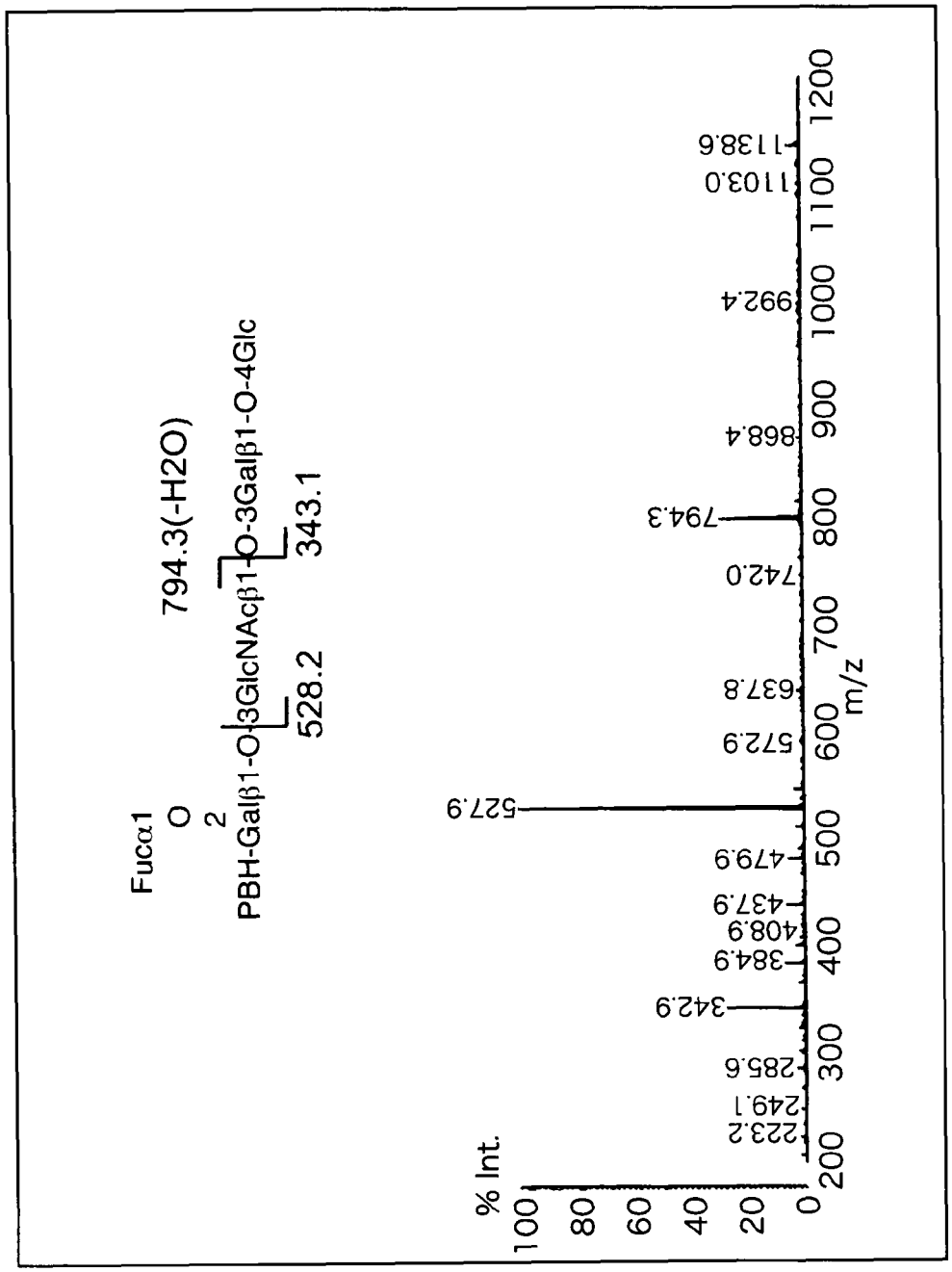
FIG. 9 is a diagram illustrating a negative-ion MALDI-TOF MS/MS spectrum of Compound (1)which is labeled and reduced at non-reducing terminal, with positions of fragmentation thereof, obtained in Example 6.
Figure 10:
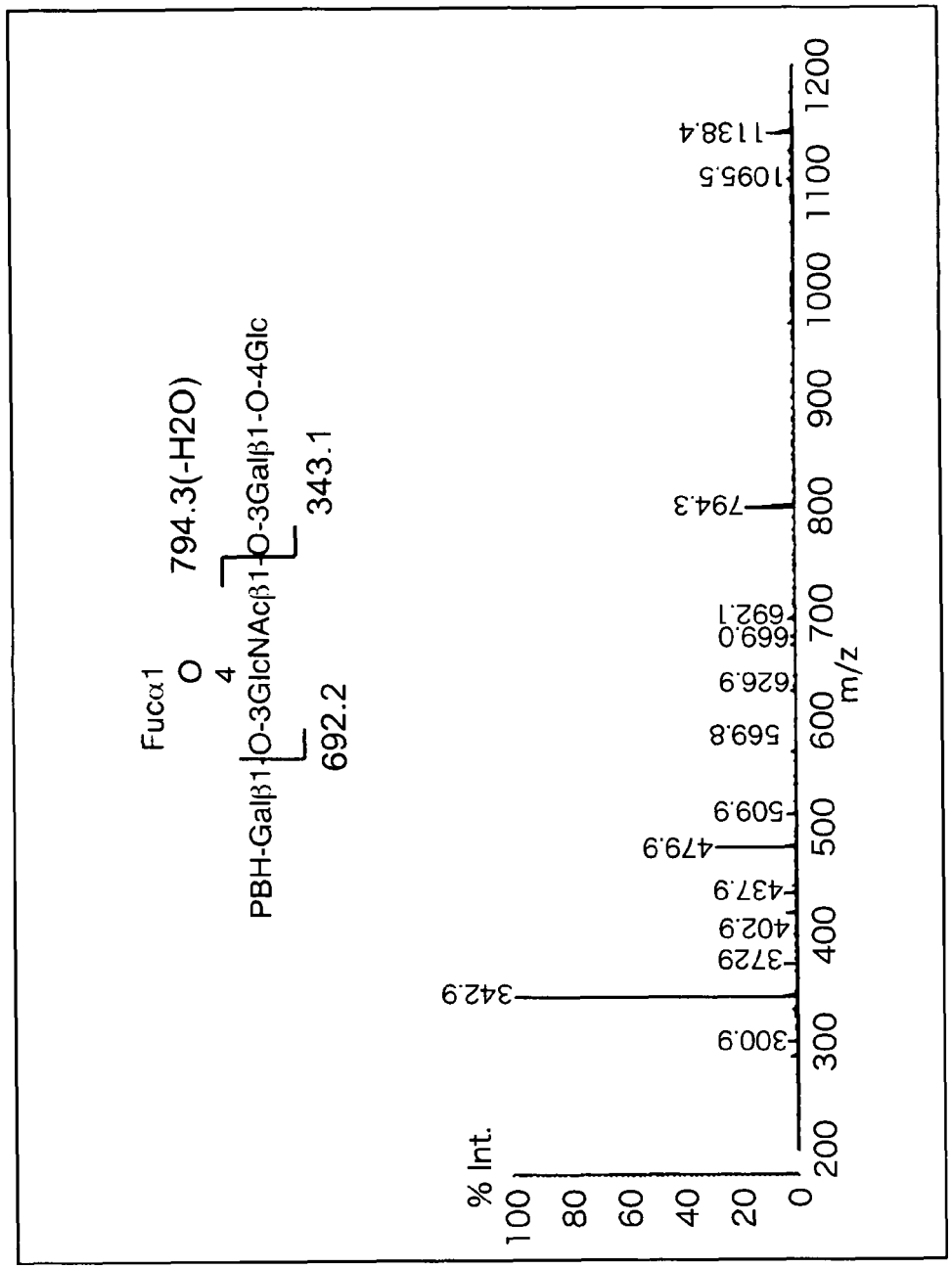
FIG. 10 is a diagram illustrating a negative-ion MALDI-TOF MS/MS spectrum of Compound (2)which is labeled and reduced at non-reducing terminal, with positions of fragmentation thereof, obtained in Example 6.

The negative-ion MALDI-TOF MS/MS measurement was carried out using the [M–H]⁻ ion having a m/z of 1138 as the precursor ion and the MALDI-QIT-TOF MS (Axima-QIT (Shimadzu/Kratos)). FIGS. 9 and 10 show the spectrum obtained from the measurement of the LNF-I and the LNF-II with positions of fragmentation thereof.

As shown in FIGS. 9 and 10, an ion having an m/z of 794.3 was detected from both of the LNF-I and the LNF-II. This ion is originated from the oligosaccharide labeled and reduced by using PBH (three sugars of Fuc/Gal/GlcNAc). Since this ion was detected, it can be seen that both of the LNF-I and the LNF-II have lactosamine structures having the fucose on the non-reducing terminal. In addition, as shown in FIG. 9, an ion having an m/z of 528.2, due to liberation of the Fucα1-2Gal structure labeled by the PBH, were detected. Since the same structure was detected in Example 5, it can be seen that the disaccharide structure is liberated, even when the reducing and labeling with PBH were carried out on the reducing terminal of the oligosaccharide and the non-reducing terminal thereof. In addition, as shown in FIG. 10, an ion having an m/z of 692.2 and an ion having an m/z of 343.1 were detected from the LNF-II labeled with PBH and reduced. The detection of these ions shows that the fucose is bonded to N-acetylglucosamine.

As described above, it is possible to analyze the blood group antigen existing on the non-reducing terminal, by carrying out the reducing and labeling of the oligosaccharide on the non-reducing terminal by means of the pyrene derivative compound. Where the glycoprotein is analyzed, it is possible to reduce and label the oligosaccharide by means of the method without liberating the oligosaccharide from the glycoprotein. Accordingly, according to the method, it is possible to improve the ionization efficiency of the glycoprotein and to analyze the oligosaccharide moiety without modification.

The invention claimed is:

1. A method for mass spectrometry for a molecule, wherein the molecule is selected from the group consisting of a saccharide, which contains an aldehyde group at the reducing terminal, and an oligosaccharide, which contains an aldehyde group at the reducing terminal, the method comprising the steps of:
   (1) labeling the aldehyde group of the reducing terminal of the molecule by means of a pyrene derivative compound having a pyrene ring and a hydrazide group or an amino group to obtain a labeled intermediate;
   (2) reducing the labeled intermediate to obtain a labeled and reduced molecule; and
   (3) carrying out MS$^n$ (n>1) analysis for the labeled and reduced molecule, with the proviso that the pyrene derivative compound has zero net charge.

2. The method for mass spectrometry according to claim 1, wherein the pyrene derivative compound is selected from the group of 1-pyrenebutanoic acid hydrazide, 1-pyreneacetic acid hydrazide, 1-pyrenepropionic acid hydrazide, aminopyrene, 1-pyrenemethylamine, 1-pyrenepropylamine, and 1-pyrenebutylamine.

3. A method for mass spectrometry for a molecule, wherein the molecule is selected from the group consisting of a saccharide, which contains a sialic acid or a non-reducing terminal galactose, and an oligosaccharide, which contains a sialic acid or a non-reducing terminal galactose, the method comprising the steps of:
(1) oxidizing only the sialic acid or the non-reducing terminal galactose of the molecule to obtain an oxidation product containing an aldehyde group;
(2) labeling the aldehyde group of the oxidation product by means of a pyrene derivative compound having a pyrene ring and a hydrazide group or an amino group to obtain a labeled intermediate;
(3) reducing the labeled intermediate to obtain a labeled and reduced molecule; and
(4) carrying out $MS^n$ (n>1) analysis for the labeled and reduced molecule, with the proviso that the pyrene derivative compound has zero net charge.

4. The method for mass spectrometry according to claim 3, wherein the pyrene derivative compound is selected from the group of 1-pyrenebutanoic acid hydrazide, 1-pyreneacetic acid hydrazide, 1-pyrenepropionic acid hydrazide, aminopyrene, 1-pyrenemethylamine, 1-pyrenepropylamine, and 1-pyrenebutylamine.

* * * * *